United States Patent [19]
Weng et al.

[11] Patent Number: 5,588,435
[45] Date of Patent: Dec. 31, 1996

[54] SYSTEM AND METHOD FOR AUTOMATIC MEASUREMENT OF BODY STRUCTURES

[75] Inventors: Lee Weng, Issaquah; Wayne Gueck, Redmond, both of Wash.

[73] Assignee: Siemens Medical Systems, Inc., Iselin, N.J.

[21] Appl. No.: 561,759

[22] Filed: Nov. 22, 1995

[51] Int. Cl.⁶ .................................................. A61B 8/00
[52] U.S. Cl. .................................................. 128/660.07
[58] Field of Search .................... 128/660.01, 660.02, 128/660.04, 660.05, 660.06, 660.07, 660.1, 661.01, 661.1

[56] References Cited

U.S. PATENT DOCUMENTS

| | | | |
|---|---|---|---|
| 4,986,274 | 1/1991 | Stephens | 128/660.07 |
| 5,211,169 | 5/1993 | Freeland | 128/661.1 |

*Primary Examiner*—George Manuel
*Attorney, Agent, or Firm*—Jeffrey Slusher

[57] ABSTRACT

Human body structures, for example, of a fetus, are automatically measured using ultrasound by first using an ultrasonic transducer or prestored ultrasound scan to generate an image frame as a pattern of pixels. Each pixel has a brightness value corresponding to an echo signal from a corresponding portion of an interrogation region of the patient's body, which includes the body structure. The image frame is displayed on a screen and includes a structure frame portion that corresponds to the body structure. The user then designates a general geometry feature of the displayed body structure and at least one measurement parameter associated with the designated geometry feature. For curved, closed structures such as the head or abdomen, the measurement parameters may, for example, be the circumference or at least one diameter. For mainly straight structures such as the femur or humerus, the measurement parameter will normally be the end-to-end length. Next, the user selects at most two reference points associated with the displayed body structure. A processing system then filters the displayed image to identify the structure frame portion, generates an approximating function corresponding to the designated measurement parameter, and calculates each measurement parameter as a predetermined function of the approximating function. The processing system preferably uses weighting, binarization and morphologic filtering of the image before generating the approximating function. The calculated measurement parameters are then preferably displayed or otherwise recorded so that the user can see and evaluate them.

8 Claims, 6 Drawing Sheets

FIG. 6

SYSTEM AND METHOD FOR AUTOMATIC MEASUREMENT OF BODY STRUCTURES

BACKGROUND OF THE INVENTION

1. Field of the Invention

This invention involves a system and a method for automatically measuring a length or other distance parameter of a body structure based on an image of the structure, in particular, where the structure is imaged using ultrasound.

2. Background of the Invention

During ultrasonic examinations, clinicians often want to measure some feature of the patient's body. This is particularly common in obstetric examinations where the sonographer often wishes to measure such things as the fetus's femur length (FL), humerus length (HL), head circumference (HC), abdominal circumference (AC), occipitofrontal diameter (OFD—the length of the line segment that lies between the left and right halves of the brain and connects opposing points of the skull), and biparietal diameter (BPD—the longest line segment with endpoints on the midpoints of the skull that is perpendicular to the line of the OFD).

There are, accordingly, several known ultrasound-based devices that incorporate some way to measure linear or arc length of structures in a patient's body. In most of these known systems, the user first looks at the ultrasound machine's display screen to determine which portion corresponds to the structure of interest. She then moves a trackball or mouse to position a cursor along this displayed structure and "clicks" on or otherwise marks various points along the displayed image. The processing system then "connects the dots" in software to form an approximate representation of the structure. and estimates the length according to some predetermined measure. Another common procedure is to mark a diameter of an approximating ellipse and to then use a repeat toggle to "open" the ellipse to approximate the circumference of a structure.

One big disadvantage of such known systems is that it takes a lot of time for the operator to define the structure of interest—in order to get a usefully accurate representation of, say, the fetus's head, the user may need to mark tens of points. Studies of obstetric sonography have indicated, for example, that 20–30% of the operator's time is taken up by performing routine measurements. Moreover, the accuracy of the measurements will depend on how carefully the user marks the displayed structure of interest and it is known that measurement results can vary greatly depending on the sonographer.

One way that has been proposed to speed up the measurement process is to automate it, allowing the ultrasound machine's processing system itself to identify and then measure the structure of interest. Common to such proposals, however, is that they treat obstetric ultrasound images as any other images, and they apply conventional image-processing techniques to extract image features for measurements. These approaches ignore the fact that it takes a great deal of computational effort for a system to identify structure that a human viewer can identify at a glance, often much more accurately than the machine, especially in the presence of significant image noise. Furthermore, the accuracy and robustness of these systems is questionable since image features can change significantly from one image to another, and can deteriorate rapidly when image quality is poor.

These proposals for fully automatic identification and measurement thus ignore how human operators can consistently perform these measurements, even for images with poor quality. For example, abdominal circumference (AC) is one of the most difficult obstetric measurements because of poor tissue boundary definition, yet human operators can usually readily identify the structure and mark reference points for the measurement routines.

Yet another disadvantage of known systems is that they use approximating functions such as best-fit circles, ellipses and line segments that introduce more error than is desirable—few heads have a perfectly circular or elliptical cross-section, and few femurs are perfectly straight. Deviations from the assumed ideal translate to measurement errors.

What is needed is a way to identify and measure body structures fast, but that still incorporates the user's ability to quickly identify features visually as well as other experiential knowledge of the shape of the structures of interest.

SUMMARY OF THE INVENTION

According to the invention, human body structures, including those of a fetus, are automatically measured using ultrasound by first using an ultrasonic transducer or pre-stored ultrasound scan to generate an image frame as a pattern of pixels, each pixel having a brightness value corresponding to an echo signal from a corresponding portion of an interrogation region of the patient's body, which includes the body structure. The image frame is displayed on a screen and includes a structure frame portion that corresponds to the body structure.

The user then designates a general geometry feature of the displayed body structure and at least one measurement parameter associated with the designated geometry feature. For curved, closed structures such as the head or abdomen, the measurement parameters may, for example, be the HC, AC, OFD, or BPD. For mainly straight structures such as the femur or humerus, the measurement parameter will normally be the end-to-end length. Next, the user selects at most two reference points associated with the displayed body structure.

A processing system then filters the displayed image to identify the structure frame portion, generates an approximating function corresponding to the designated measurement parameter, and calculates each measurement parameter as a predetermined function of the approximating function.

The calculated measurement parameters are then preferably displayed or otherwise recorded so that the user can see and evaluate them.

BRIEF DESCRIPTION OF THE DRAWINGS

FIG. 6 illustrates the operation of certain morphologic filtering rules applied to binarized images.

DETAILED DESCRIPTION

Figure 1:
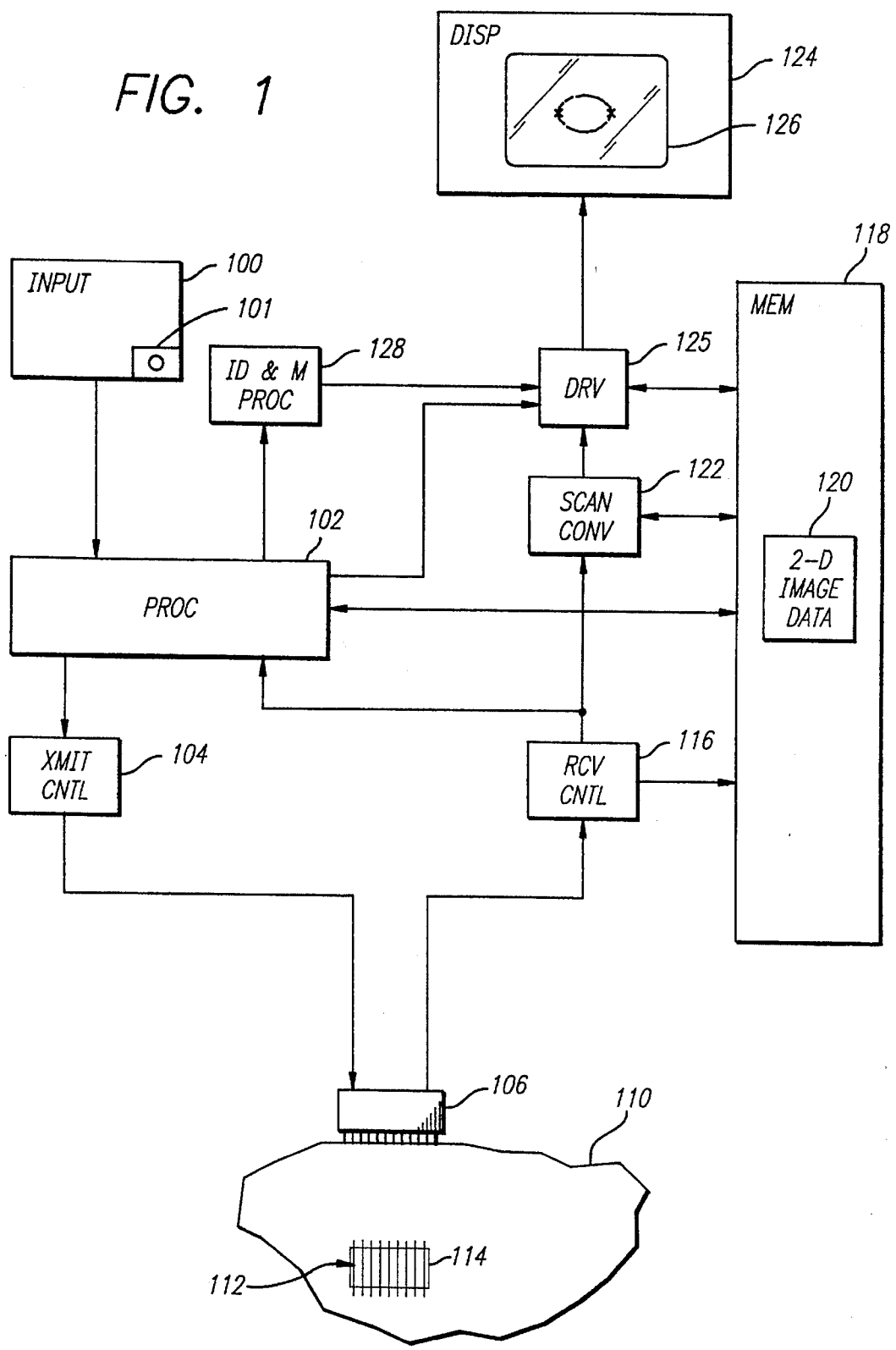
FIG. 1 is a block diagram of an ultrasonic imaging system with an identification and measuring processor and display according to the invention.

FIG. 1 illustrates the main components of an ultrasonic imaging system according to the invention. The user enters various conventional scan parameters into an input unit 100, which typically includes such devices as a keyboard, knobs, and buttons, and a cursor-control device such as a trackball 101 or mouse. The input unit is connected to a processing system 102, which will typically be an electrically connected and cooperating group of processors such as microprocessors, digital signal processors, and application-specific integrated circuits (ASIC); the processing system may, however, also be implemented by a single processor as long as it is fast enough to handle the various tasks described below.

As in known systems, the processing system 102 sets, adjusts, and monitors the operating parameters of a conventional transmission control circuit 104, which generates and applies electrical control and driving signals to an ultrasonic probe 106, which includes an array of piezoelectric elements. As is well known in the art, the piezoelectric elements generate ultrasonic waves when electrical signals of the proper voltage and frequency are applied to them.

By placing the probe 106 against the body of a patient, these ultrasonic waves enter a portion 110 of the patient's body. By varying the phasing, amplitude, and timing of the driving signals, the ultrasonic waves are focussed to form a series of scan lines 112 that typically fan out from the probe. Several such scan lines are shown extending into the patient's body in FIG. 1. A region of interest, that is, the region that the user wants to have an image of, is shown as an interrogation region or volume 114. The manner in which ultrasonic scanning signals are controlled, generated, and applied to a patient's body is well understood in the art and is therefore not described further.

Ultrasonic echoes from the waves transmitted into the body return to the array in the probe 106. As is well understood, the piezoelectric elements in the array thereby convert the small mechanical vibrations caused by the echoes into corresponding electrical signals. Amplification and other conventional signal conditioning is then applied to the return signals by a reception controller 116. This processing includes, as needed, such known signal conditioning as time-gating, gain compensation, and noise filtering, in order to identify the echo signals that correspond to the interrogation region 114.

The reception controller 116, all or part of which is normally integrated into the processing system 102 itself, processes the ultrasonic, radio-frequency (RF) echo signals from the array (typically on the order of a few to tens of megahertz) to form reception beams along the transmission beam direction. This is well known in the art of ultrasonic imaging. The magnitude values of the received beams for the two-dimensional interrogation region are stored digitally in a memory 118 as 2-D frame data 120. Each set of frame data corresponds to one image frame, that is, to a 2-D cross section of the interrogation region.

The stored data format is normally not in the same shape or size as what the user wants to see displayed. The echo magnitude values for an image frame are therefore applied to a conventional scan converter 122, which converts the stored image into a display format that is suitable for use in driving a display device 124. The display device 124 typically includes a conventional display driver 125 and a screen 126 (for example, LED or CRT) that is divided into an X-Y (or polar) matrix or pattern of picture elements or "pixels" that make up an image that the user can view and interpret.

The image is displayed as a pattern of image elements that correspond to the received echo magnitude from corresponding portions of one 2-D frame of data from the interrogation region. Note that a displayed image element will often be made up of more than one pixel, but that this will depend on the relative resolutions of the scan and of the display. The invention does not require any particular relative resolution.

Ultrasonic imaging may be done in any of several modes. One common mode is the brightness or "B" mode, in which the display is typically gray-tone, and the displayed intensity of each pixel corresponds to the amplitude of the echo signal from a corresponding element or portion of the interrogation region. In other words, the stronger the acoustic echo is from a portion of the scanned region, the more brightly it is displayed. Note that it is also possible to display intensity data using "pseudo-colors," that is, such that different intensities (or intensity intervals) are displayed using different assigned colors. For example, increasing intensity can be displayed as increasingly more red.

The invention also includes a feature identification and measurement (ID&M) sub-system 128, which is connected to or receives positional signals from the cursor control device (preferably, trackball) 101, the display driver 125, and the memory 118 in order to access the 2-D frame data 120. Connection with other system components such as the display driver and memory may be either direct or indirect via some other component such as the general processing system 102 or a dedicated intermediate circuit. The ID&M sub-system may be a separate processor or cooperating group of processors; alternatively, it may be combined with or incorporated in some other processors in the system.

The general method according to the invention includes the following main steps:

1) The user selects an image for display on the screen 126.
2) The user marks reference points on the display depending on a user-specified assumption about the general geometry of the body structure of interest.
3) The system applies a series of conversions, filters, and other procedures to the image, identifies the structure, and automatically measures the parameter of interest, which will normally be the path length of an approximate line segment (for example, for a femur) or a measure of circumference, diameter, or even area of a closed region such as a cross-sectional display of the skull.

These steps are explained in detail below.

Image Selection

During the normal course of an ultrasound scan, the user will view the display screen 126, which will display the series of frames corresponding to the scan. When the body structure of interest is visible on the screen, the user then directs the system to "freeze" the displayed data frame; the user may do this in any known manner, such as pushing or releasing a button, switch or key on the probe 106 or input device 100. Alternatively, using known methods, the user may call up a pre-stored frame of image data from an earlier scan. It is also possible according to the invention to allow the system to generate continuously updated measurements, with no need to stop the scan to "freeze" a frame, as long as sufficiently fast processors are included in the system.

Reference Point Marking

It is known to display a cursor on a screen, such as the display screen 126. According to the invention, the user first maneuvers the input device (preferably, a mouse or the trackball 101) to move a cursor on the display screen until it points to or lies on a first reference point on the displayed structure of interest. She then activates a button, key or other known switching device to signal to the processing system 102 that the corresponding first reference image element is at the first reference point, and the processing system, via the display driver, then displays a suitable mark, such as an "X", cross-hairs, etc., at this point. The user then repeats this process to select and have marked a second reference point on the displayed image, corresponding to a second reference image element. Note that the scale of the image is known to the system and is also normally displayed along one edge of the screen. It is consequently possible for the system to apply known methods to calculate the linear distance between any two given points on the display screen.

The preferred criterion for selecting reference points depends on the assumed general geometry of the body structure of interest; the various criteria are described in detail below. One should note, however, that it is not necessary for the user to define the entire structure to be measured by marking dots all along its path. Rather, in the preferred embodiment of the invention, the user needs to designate at most two delimiting reference points; indeed, in certain embodiments, the system according to the invention can operate fully automatically and determine the length parameter of interest with no user-input of reference points at all. The system according to the invention then automatically determines the remaining image points necessary to calculate the parameter of interest, and performs the calculation. Since the processing systems 102 and 128 may operate many orders of magnitude faster than can a human operator who is "clicking" on a large number of image points, the invention greatly speeds up the process of measuring the displayed body structure; furthermore, it produces more consistent and unbiased measurement results than what a human operator can.

According to the invention, it is preferably assumed that the body structures of interest will have either of two general geometries: mainly closed and round or mainly open and linear. Measurements of generally closed, round structures would include measurements of head circumference (HC) and abdominal circumference (AC). According to the invention, other features such as biparietal diameter (BPD) are essentially linear, but characterize a generally closed, round structure and are determined using procedures for such round structures. One example of a measurement of a generally open and linear structure would be the measurement of femur length (FL).

Note that body structures such as the head and femur will seldom if ever be perfectly "round" or "straight," respectively. The invention does not require them to be and, indeed, can in most normal cases even "fill in" gaps in the image as long as the general shape is known.

The user may specify the assumed general geometry in any of several different ways. Examples include keyboard entry and cursor-controlled selection from a displayed menu, pull-down menu, or icon group giving the selection for the possible general geometries. The geometry selections could be words describing the general shape, such as "STRAIGHT," "ROUND," or "LINE," "CIRCLE," etc.; of the structure itself, such as "FL," "HC," "BPD," etc.; or, especially in the case of an icon group, even symbolic choices such as small pictures of line segments, circles (for circumference), diameters of circles, or shaded circles (for area calculations).

In a conventional ultrasound scan, the areas of the interrogation region with the strongest return signals are usually displayed brighter (closer to the white end of the gray scale) than areas with weaker return signals; bright areas typically correspond to body structures, since structural boundaries tend to have relatively large changes in acoustic impedance. Most of the image looks "dark." To make it easier to see features against the white background of the drawings, this shading scheme is reversed in those drawings that illustrate scan images, so that areas with stronger return signals are shown darker.

Round Structures

The two most common closed structures of interest in obstetric ultrasound examinations are the head and abdomen of the fetus and the parameters of greatest interest are the circumference (HC and AC) and some diameter (in the case of the head, BPD and OFD). The invention measures such mainly closed structures in substantially the same way, although, as is described further below, it is also able to make use of additional known structural features of the fetal brain to improve the ability to identify and measure the skull.

The main steps the invention follows for measuring closed structures are as follows:

1) The assumed image of the structure is delimited to a portion of interest.

2) The delimited portion is converted from the raster form in which it is normally displayed into a polar form for analysis.

3) After optional but preferred sub-steps such as contrast enhancement and weighting, the polar image is binarized so that all image elements are preferably rendered as either fully "white" or fully "black."

4) The binarized image is filtered morphologically to further isolate the image elements that correspond to the closed structure.

5) Curve boundaries are identified, filtered, and filled in as needed to form a filtered representation of the structure.

6) An optimal approximating boundary function is determined and displayed for the filtered representation, and its length (corresponding to the circumference) is calculated and displayed.

7) If the length parameter of interest is a diameter, such as AD, BPD, or OFD, then this is determined by evaluating the boundary function.

These steps are explained further below.

Figure 2:
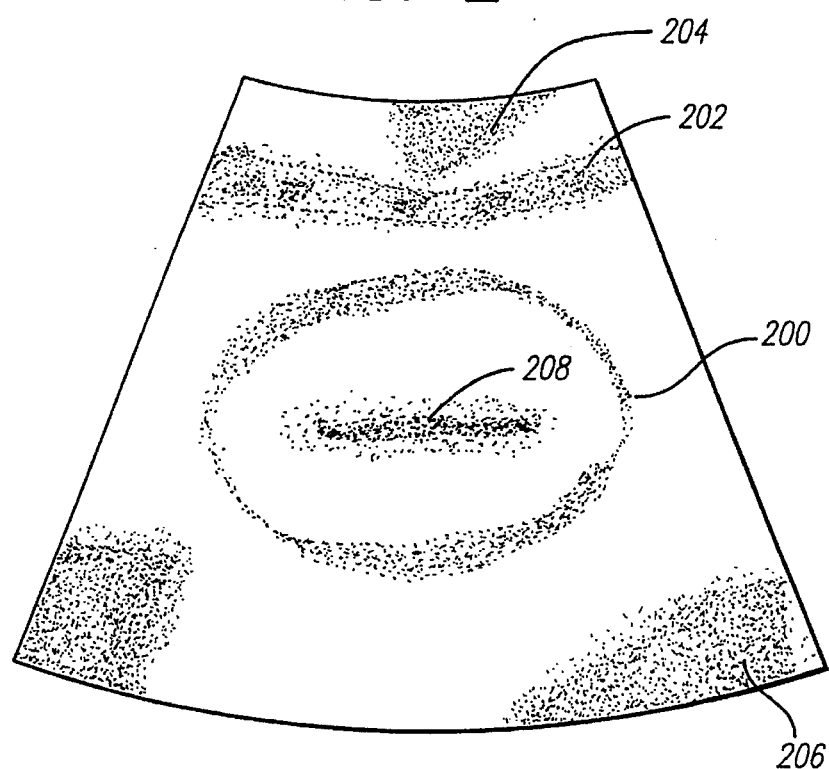
FIGS. 2 and 3 illustrate an ultrasonic scan of a cross section of a head without and with, respectively, user-selected reference points and system-generated delimiting curves.

FIG. 2 illustrates an image of an ultrasound scan of a cross-section of the head of a fetus. The skull appears as a generally elliptical closed region, which, because of noise, deflection, and other acoustic properties of the interrogation region, may have "breaks," for example, often where the surface is parallel to the direction of propagation of the ultrasonic scanning signals. The image will often also have visible returns from relatively structured regions, which themselves have a pronounced curved or linear shape. These might, for example, be returns from the mother's own muscle tissue or uterine wall 202, or from fat layers 204. Other visible returns may appear generally unstructured, such as the region labelled 206 in the figure. All such returns are irrelevant (they are noise) to measuring any distance parameter of the head and their influence should therefore be eliminated or at least reduced; the way in which the invention does this is described below.

Examinations of the head usually also have a visible return from the mid-line 208, that is, the substantially linear region between the two hemispheres of the brain. Although the invention is able to determine head circumference and different diameters without mid-line information, the preferred embodiment isolates the mid-line image and uses the corresponding image portion to improve its ability to identify and measure diameters.

Notice that most structured noise is located outside the generally elliptical curve of the skull, whereas the midline is located inside the curve. Notice that the skull usually more closely approximates an ellipse than a circle, and that it may "bulge" more at the rear than at the front. The way in which the invention uses these properties to advantage is described further below.

Figure 3:
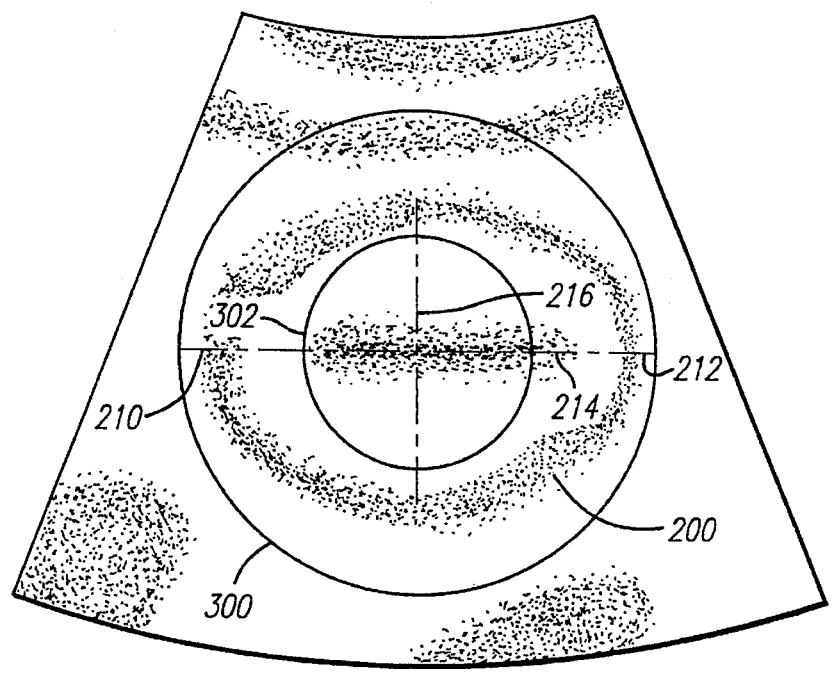

FIG. 3 illustrates the same scan as FIG. 2, but shows certain system-generated display features such as the references points 210, 212 (indicated as small crosses "+"), which the user selects in the manner described above, as well as an OFD line 214 and a BPD line 216. As is well known, the OFD line lies on or very close to the mid-line 208. The invention preferably also generates and displays a line of circumference, which shows the circumference that the invention determined based on the image and used in measuring circumferential or diametral length. This line is preferably superimposed on the display, but is not drawn in FIG. 2 to avoid confusion with the skull image 200. The lines 214, 216 and the circumference line are preferably displayed in a non-gray scale color so that the user can see clearly where and what they are.

For head or abdominal measurements, the user should preferably mark as reference points 210, 212 the approximate endpoints of what she estimates to be the major axis (greatest diameter) of the curve 200. As is explained below, this aids the invention not only by identifying two points assumed to lie on or very near the curve 200, but also by setting a rough upward bound on the diameter of the curve. The user could, however, also be instructed to mark the assumed endpoint of the minor axis of the curve, which would set a rough lower bound on the size of the curve. Some other pair of reference points, preferably diametrically opposing, could also be marked, but such a choice will in most cases not give as useful a starting "guess" to the system. Furthermore, according to one alternative embodiment of the invention, the system can isolate the curve 200 based on only a single point (preferably near the center of the curve).

Any conventional coordinate system and scale may be used according to the invention to define, both quantitatively and qualitatively, such terms as "inside," "outside," as well as distances. The position of any point in the interrogation region is therefore well-defined in known system coordinates.

Structure Delimitation

In the preferred embodiment of the invention, the curve 200 is delimited by an outer circle 300, whose radius is at least as large as the largest possible radius of the curve 200, and an inner circle 302, whose radius is at most as large as the smallest possible radius of the curve 200. There are several ways according to the invention to determine the radii of the delimiting circles 300 and 302.

In the preferred embodiment, in which the user is instructed to choose the reference points 210, 212 to be the endpoints of the major axis of the curve 200, the invention first designates an assumed center point at the midpoint between the two reference points 210, 212. The distance from the midpoint to either reference point is then the reference radius $r_{ref}$. The radii of the outer and inner circles can then be set equal to predetermined percentages greater than and less than, respectively, $r_{ref}$. The percentages will depend on the assumed maximum eccentricity of a head (or abdomen or other generally round structure of interest), which can be determined by experiment. Alternatively the system may include and use a pre-stored table of known, maximum outer radii (for example, OFD for the head) for a fetus at any given gestational stage. The user may then enter the approximate gestational stage, for example, in weeks, before the system begins the measurement procedure.

As one alternative, it will often be adequate simply to set the radius of the outer circle equal to $r_{ref}$ plus some predetermined small margin, that is, to let the circle pass just on the outside of the reference points. Rather than using percentages, the radius of the inner and outer circles may alternatively be set to a distance corresponding to an experimentally predetermined number of pixel values inside and outside the references marks, measured along the line 214.

It is also possible, however, not to require or rely wholly on such prior knowledge of eccentricity. Instead, the invention may divide the entire image region into several angular sectors, and then divide each angular sector into several concentric, radial tracks. In order to reduce the size of the irrelevant area about the midline 208, the sectors may have a minimum radial boundary set to an experimentally predetermined percentage of the major radial distance. Alternatively, the system can calculate the minimum radial boundary to be greater than half the length of the midline 208 (see FIG. 1), which may be identified and measured using a routine described below. To avoid the possibility that this value is too large (greater than the possible BPD), an upper limit for the minimum radius may be set as a percentage of the distance $r_{ref}$.

Related to this alternative implementation, the number of sectors and the radial width of the tracks may be chosen by experiment. The average intensity of each track is then calculated and the radius of the innermost peak average intensity for each sector is identified. The maximum and minimum peak radii are then also identified. The radius $r_{min}$ of the inner circle 302 can then be set to a value that is less, by a preset percentage, than the smallest "peak" radius. Similarly, the radius $r_{max}$ of the outer circle 300 can be set to a value that is greater, by a preset percentage, than the greatest "peak" radius. The greatest innermost radius should be approximately equal to an experimentally predetermined percentage of the reference radius $r_{ref}$. Furthermore, for heads, the radius to the innermost peak should be for the sector that extends roughly perpendicular to the line 214. If either of these assumptions is violated, then the system may apply default radius values determined as above based on percentages of $r_{ref}$.

Observe that delimiting the structure not only speeds up calculation times but also, usually, "automatically" cuts out much noise.

Raster-to-Polar Conversion

As is usual, the image that the system displays to the user is in the substantially Cartesian, raster format illustrated in FIGS. 2 and 3. This is natural, since it maintains the scale and shape of the actual body structures being imaged, assuming appropriate conventional beamforming and scan conversion are provided. For purposes of structure identification and measurement, however, the invention preferably converts the raster image into polar form, with the calculated center point (the midpoint of the line connecting the reference points) as the origin of the r-θ (radius-angle) polar coordinate system. It is not necessary to display the conversion to the user; rather, the intensity values of the raster scan are stored in polar form in the memory.

Figure 4:
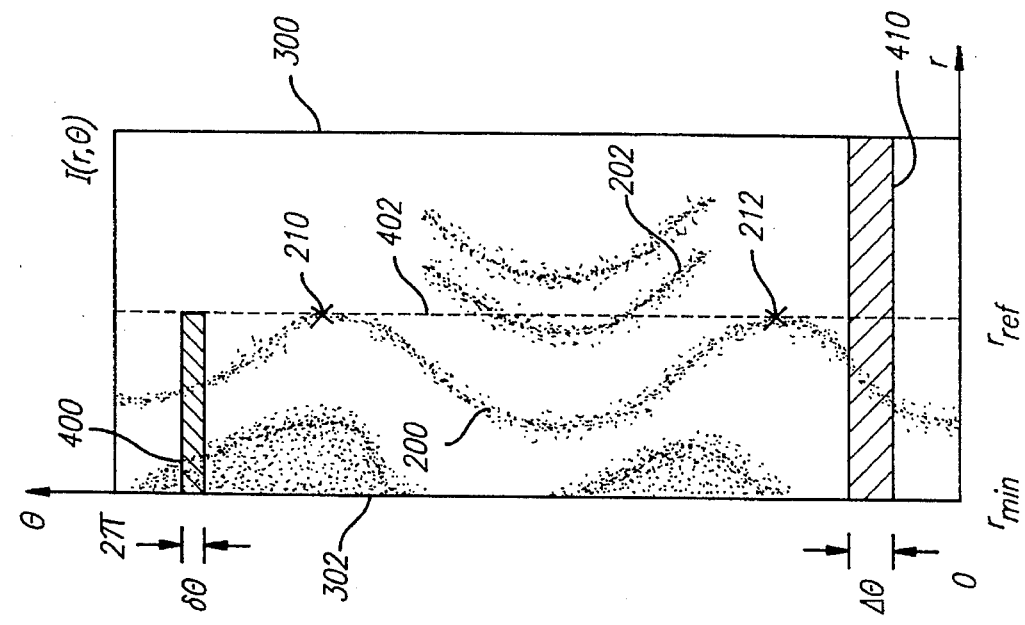
FIG. 4 illustrates raster-to-polar conversion of a delimited portion of the image in FIGS. 2 and 3.

FIG. 4 illustrates the image of FIGS. 2 and 3 in polar form. Since it is known that the curve 200 lies completely outside of the inner circle 302 and inside the outer circle 300, only this annular region is preferably converted and stored. With the chosen origin, the inner and outer circles will map to straight lines and are shown as such in FIG. 4. The curve 200 will map to a wavy, substantially sinusoidal line; the waviness of the line increases the more the curve 200 deviates from being a circle. The region between the outer and inner delimiting circles 300, 302 thus defines an annular search region for the image.

One advantage of setting $r_{min}$ and $r_{max}$ according to a number of pixels offset from the reference points is that the circle through the reference points will then map to a vertical line that divides the polar representation into halves of equal width. This is therefore preferred, although it is not necessary as long as the inner circle is chosen small enough to certainly lie fully within the curve 200. FIG. 4 is drawn to illustrate this.

It is not necessary to convert to polar representation every image element between the delimiting circles 300, 302, although this may be done if the necessary computations can be done if the additional time required to do the calculations is acceptable in a given application. Rather, the polar image illustrated in FIG. 4 may be compiled using the pixel intensity information only along a number of radial rays that extend between the delimiting circles. For example, assuming that the outer and inner circles 300, 302 are positioned m pixels beyond and within, respectively, the reference mark, and n rays are spaced evenly over the 360° extent of the annular search region, then the annular search region will map to an m-by-n pixel rectangular strip as shown in FIG. 4.

The more rays that are used, the greater will be the resolution polar representation, but the longer it will take to perform the measurement. The number of rays will therefore be determined by normal experimentation given knowledge of the processing speed available in any given application. In one prototype of the invention, 256 rays of 128 pixels in length were evaluated and convened to polar form. In FIG. 4, the r-axis would therefore represent a pixel width of 128 from $r_{min}$ to $r_{max}$ and the θ-axis would represent 256 horizontal "strips" one pixel wide, 128 pixels long, and with an angular spacing of approximately 360/256 degrees.

Image Binarization

In order to measure the curved body structure, the invention must first determine which of the pixels in the image represent the structure. After the structure has been delimited as described above, the elements in its image still have intensity values throughout the gray-scale range of the display. The invention preferably binarizes the image before further filtering and measuring.

The simplest way to binarize the image of FIG. 4 is to determine by experimentation and observation a threshold intensity value $I_t$; one can then set to full bright ("1") each image element whose intensity value is greater than $I_t$ and set all other element values to full dark ("0"). This will completely eliminate from consideration all noise below $I_t$, but in general it will be difficult to determine an absolute value for the threshold $I_t$ that will be suitable for different images or structures. For example, if an image is relatively dark (a low mean brightness), then it may be set completely to black, even though the human user herself might be able to discern the body structure in the weak image.

One improvement the invention includes is that it chooses $I_t$ to be a function of a maximum intensity value in at least a local portion of the search region. It then compares a filtered functional value of the element intensity values with $I_t$ and then sets them to full bright or full dark accordingly. The preferred ways to determine $I_t$ and to filter the image intensity values are described below.

Contrast Improvement

The first step in the binarization method in the preferred embodiment of the invention is to increase the contrast of the polar image, which is shown in FIG. 4. Common to all methods for improving contrast according to the invention is that a turning point brightness is determined. A contrast function is applied to the pixels in the polar image with the result that elements whose intensity is greater than the turning point brightness are made even brighter and elements whose intensity is less than the turning point brightness are made even darker.

One way to increase contrast is by using a single-parameter contrast function such as $I_{cont}=I_{in}^{\gamma}$ where $I_{cont}$ is the intensity of a pixel after contrast improvement, $I_{in}$ is the input intensity $I_{in}$, and $\gamma$ is an experimentally determined parameter that defines the turning point brightness. Since $0 \leq I_{in} \leq 1$ (in certain cases, after standard normalization), then $0 \leq I_{cont} \leq 1$.

Contrast functions of two or more parameters may also be used. One example is a sigmoid contrast function such as:

$$I_{cont} = \frac{1}{1+e^{-b \cdot (x-a)}}$$

where $x=I_{in}$; a is the turning point; and b determines the degree of "stretching" of the intensity values about a. The value a may, for example, be chosen equal to the average intensity of pixels in a predetermined region and b may be set equal to the standard deviation of intensity values for pixels over the same or over some other region. The preferred regions over which the average and standard deviation are determined are described below.

In FIG. 4, a constant angle image "strip" is labelled 400. The angular width δθ of the strip may be any number of pixels, but is preferably one pixel, so that the strip corresponds to a radial ray. In the illustrated example, the strip extends only to the line through the reference points at radius $r_{ref}$; this makes use of the fact that, for heads, the most useful information about the curve 200 lies in the left half plane of the polar plot, whereas the right half will typically have a much lower signal-to-noise ratio. The strip could, however, extend further, even to the outer circle 300, and preferably does so in the case of imaging of an abdomen.

For the exponential contrast function, the value of a used for the pixels in any given strip is the average intensity of the pixels in that strip. The value of b, however, is preferably a function of the standard deviation of intensity for all pixels in the left half plane (all pixels from $r_{min}$ to $r_{ref}$). The advantage of using a local mean a but a global stretching factor b standard deviation is that portions of the search region that have relatively low intensity more because of their position, for example on the side of the head away from the transducer, will not be darkened because of their position alone. The degree of "stretching," however, will be determined by the same parameter b for all pixels. Changes in contrast will therefore depend on relative brightness rather than on position.

The parameter b may differ depending on the type of examination, but will often be more or less constant for any given type. It is therefore possible according to the invention to determine these contrast "stretching" values for, for example, heads, livers, thyroids, or other structures. The system can then save calculation effort simply by using the appropriate prestored value.

Note that the values a may be determined based on only part of a radial sector, for example, the left half-plane strip 400 in FIG. 4. This value, however, is used in the contrast function that is applied to all pixels over the full $r_{min}$ to $r_{max}$ width of the corresponding $\delta\theta$ strip.

The abdomen normally doesn't have as many bright structures as the head, since the structures for the mother and fetus are roughly the same and dark regions are mostly amniotic fluid. Instead of a half-plane strip 400 as is illustrated in FIG. 4, it is preferred to evaluate the local parameter a over the entire radial strip from $r_{min}$ to $r_{max}$, or within an annular sector centered on the $r_{ref}$ line but less than the full width of the plot. The inventors have determined that two ways of choosing a that produce good results for abdominal measurements are:

$$a = \tfrac{1}{2} \cdot \mu^2$$

where $\mu$ is the average intensity value of the strip, $0 \leq \mu \leq 1$. and $$a = max[(\tfrac{1}{2}\cdot\mu^2), (\mu - \sigma_{cent}), I_{min}]$$

where $\sigma_{cent}$ is the standard deviation of intensity values within an annular strip centered on the $r_{ref}$ line extending, for example, half way to $r_{max}$ and $r_{min}$ on either side and $I_{min}$ is the minimum intensity value in the corresponding strip. For certain abdominal images, the first term ($\tfrac{1}{2}\cdot\mu^2$) can become very small and the value $\sigma_{cent}$ can become large. Although these terms provide good "stretching," that is, contrast improvement, they may occasionally provide too low a turning point to be useful. Including $I_{min}$ thus avoids having all or most pixels in a strip being set to "bright" ("1") in such cases.

For other body structures, different turning point parameters a and "stretching" parameters b may be determined by experiment. Indeed, other contrast functions may be chosen if experience with imaging a particular body structure indicates some advantageous function choice.

In order to avoid suspiciously rapid changes in the global parameter values b from one frame of measurement to the next, it is also possible to set this value equal to a weighted average of the current and one or more most recent values. For example, the system could apply as $\sigma$ the value $\sigma = \alpha \cdot \sigma_{new} + (1-\alpha) \cdot \sigma_{old}$, where $\alpha$ is chosen by experiment. Another method for smoothing these parameters is to include more lines (angles) in the neighborhood used for calculating the parameters such as $\mu$ and $\sigma$; moreover, smoothing even over such multi-angle regions may be combined with previous values using a time-decay factor such as the one described above.

Radial Weighting

Once the contrast function has been applied to all of the pixels of interest in the search region, their intensity values are preferably weighted such that the intensity value of a pixel is lower the farther it is from the $r_{ref}$ line. Note that this is spatial weighting or filtering, as opposed to purely brightness-derived weighting or filtering used in the contrast-improvement step above.

In the preferred embodiment of the invention, a Gaussian weighting function is applied over each radial strip. This is done by multiplying each intensity value by the weighting factor:

$$e^{\frac{-(r-r_{ref})^2}{2\cdot s}}$$

where r is the radial distance of the pixel from the center point and s is an experimentally determined roll-off factor. Note that the pixel on the $r_{ref}$ line retain their intensity values whereas pixels at the edges of the search region (from $r_{min}$ to $r_{max}$) are attenuated.

Other weighting functions may of course be used, such as triangular, trigonometric, or parabolic windows. Furthermore, the weighting calculations may be combined with those for contrast improvement.

Binarization Threshold

After the preferred but optional steps of contrast improvement and weighting, the image is still in a gray-tone format, that is, the pixel intensity values are distributed over a range of brightness. The final step in binarizing the image is to select the threshold intensity value $I_t$ and apply the threshold to the pixel intensity values so that the remaining image consists of pixels whose values are either full bright ("1") or full dark ("0").

One way to select $I_t$ is as a global value. For example, the system may evaluate the pixel intensity values for all pixels in the search region to determine the maximum intensity $I_{max}$. All pixels whose intensity value is greater than or equal to an experimentally predetermined percentage of $I_{max}$, for example, $0.7 \cdot I_{max}$ are then set to "1" and all whose values are less than this value are set to "0".

In order to make the binarization less sensitive to general image brightness and more robust in different image regions, the invention preferably uses an adaptive threshold technique: First, the image is preferably divided into p radial strips with an angular width of $\Delta\Delta$ degrees ($\Delta\theta = 360/p$). In FIG. 4, one such strip is labelled 410. The number p in one prototype of the invention was set to ten, which is equivalent to dividing the image into 36 "pie slice" sectors. Note that it will in general not be necessary to have the strips as narrow as a single pixel; the number p may be chosen by experiment for any given application.

In the following discussion, $I(r,\theta)$ is the intensity value (after contrast improvement and weighting, if these steps are included) of the pixel at the position $(r,\theta)$.

First, the system evaluates the pixel intensity values $I^{(i)}(r,\theta)$ in each strip to determine the maximum value $I_{max}^{(i)}$ for strip i. It then compares $I_{max}^{(i)}$ with an experimentally pre-set minimum acceptable intensity level $I_{min}$. If $I_{max}^{(i)} < I_{min}$, then all of the pixel values in strip i are set to "0", since this condition indicates that the strip as a whole is so dark compared with experimentally expected intensity levels that it contains little information about the structure to be measured.

If however, $I_{max}^{(i)} > I_{min}$, then the system assigns binarized pixel intensity values $I_b^{(i)}(r,\theta)$ as follows for the pixels for each strip i:

$$I_b^{(i)}(r,\theta) = 1 \text{ if } I^{(i)}(r,\theta) \geq k \cdot I_{max}^{(i)}$$
$$= 0 \text{ otherwise}$$

where k is a preset cut-off factor that, in one prototype of the invention, was 0.7, but that can be determined by experiment for any given application and type of examination.

Morphologic Filtering

Figure 5:
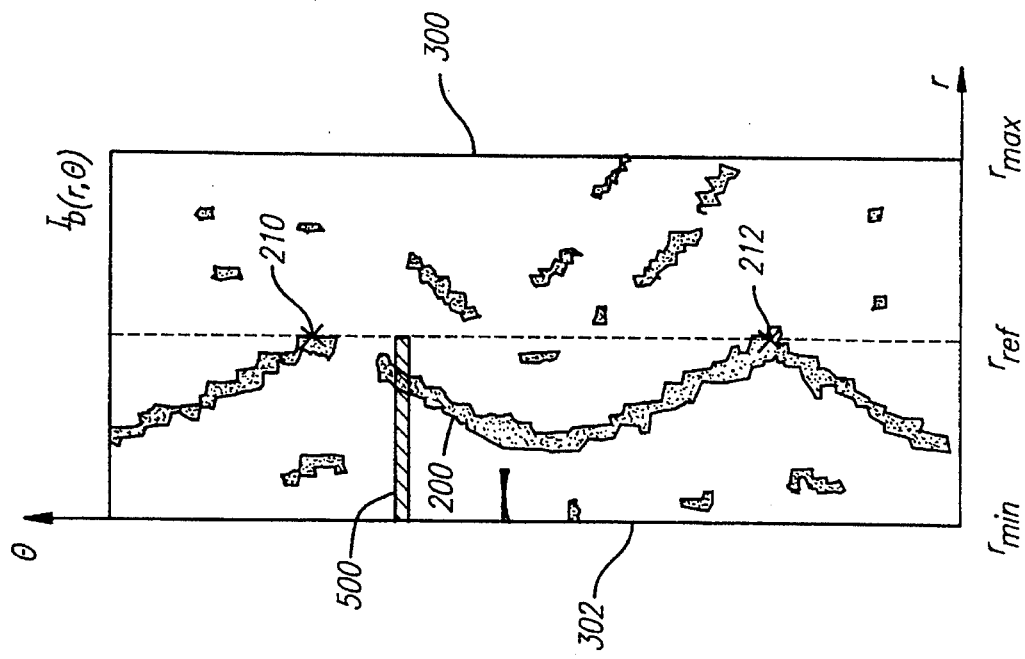
FIG. 5 shows the polar image of FIG. 4 in a binarized form.

FIG. 5 illustrates the general appearance of an image such as the one shown in FIG. 4 after binarization according to the invention. As one can see, noise in the original gray-scale image can produce some small isolated bright spots in the binary image. The noise also makes the edges of the expected boundaries rougher than they should be. Furthermore, some irrelevant small image features may also appear as isolated spots in the binary image. To remove these isolated spots and to make the expected boundaries more smooth and continuous, the system according to the invention applies a series of morphologic filters to the binarized image. These morphologic filters, which are described below, make use of the knowledge that the expected boundaries should be thick and smooth.

Figure 6:
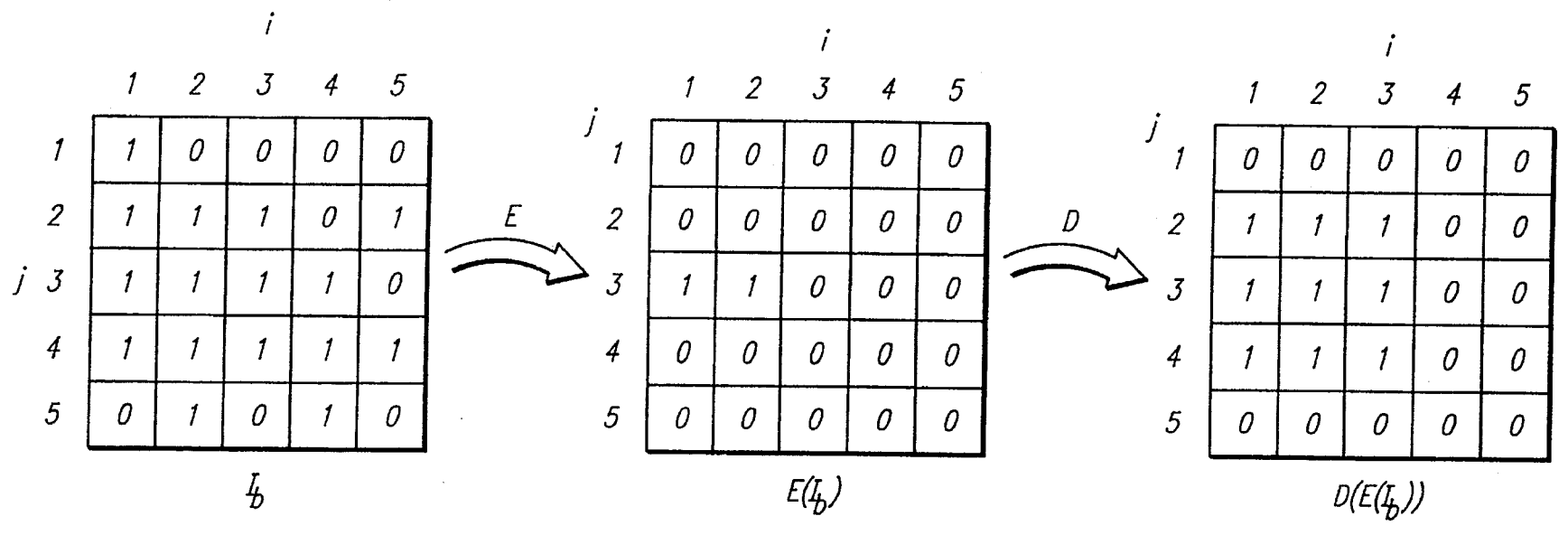

FIG. 6 shows a 5×5 pixel portion of the binarized image $I_b$; what the image looks like after one application of a morphologic erosion rule E to form $E(I_b)$; and what the once-eroded binarized image portion looks like after one application of a dilation rule to form $D(E(I_b))$. For ease of illustration and explanation only, the pixel portion in shown as a row-column (i,j) of pixels; for example, $I_b(2,3)=1$ and $I_b(3,5)=0$. Note, however, that the binarized image is still in polar form. The morphologic rules are of course applied to the entire binarized image $I_b$; the 5×5 pixel portion simply illustrates the procedure.

Each pixel in the pattern has several neighboring pixels. For example, pixel (2,2) has neighbors (1,1), (1,2), (1,3), (2,1) (2,3), (3,1) (3,2), and (3,3). According to the erosion rule, a pixel's value is set to zero if the value of z of its neighboring pixels is zero. According to the dilation rule, if a pixel's value is "1", then u of its neighbors' values are set to "1". For the row-column pattern in FIG. 6. The parameters z and u may be chosen by experiment to yield thick, smooth boundaries. In one prototype of the invention, however, the inventors have discovered that good boundaries can be had using the simplest erosion and dilation rules, that is, z=1 and u=8. In other words, in the implemented embodiment of the invention, the erosion rule was that a pixel's value was set to "0" if the value of even a single neighbor was "0" and the dilation rule was that, if a pixel's value was "1", then the values of all neighbors were set to "1".

The center frame of FIG. 6 shows the application of this erosion rule E on $I_b$ to form $E(I_b(i,j))$: only the pixels $I_b(3,1)$ and $I_b(3,2)$ "survive" in the eroded frame. The right frame of FIG. 6 shows the application of the dilation rule D to form $D(E(I_b(i,j)))$. Even in this simple illustration one can see how the chosen morphologic rules make the image more uniform, with fewer "rough" edges.

Other morphologic rules may be used according to the invention and other pixel patterns are possible. For example, it is also possible to use known gray-tone morphologic rules directly on the unbinarized image, and one could expand the concept of the pixel "neighborhood" to include non-adjacent pixels. Moreover, although it is preferable to erode $I_b$ before dilating it, since this most sharply defines boundaries, it is also possible according to the invention to perform these operations in reverse order as long as the values z and u are chosen by experiment so as not to thicken "noisy" boundaries too much.

As for pixel patterns, although the row-column pattern is normally easiest to implement, one could, for example, also have staggered rows, so that each pixel is in the center of a hexagonal neighborhood. The most easily implemented representation for $I_b$ will typically depend on the pixel pattern of the display screen used.

Boundary Searching

For head circumference (HC) or abdomen circumference (AC) measurement, human operators have a clear idea when they start of what the structure looks like. The goal is to find a "circular-shape" head or abdomen in the image. First, the operators narrow their search to an area where the shape exists. Then they locate obviously good boundaries, which appear to have bright curvature with a single clear boundary. In those places where features are not clear or not visible, like in image drop-out areas, they can make a reasonable guess where these missing features should be by associating their searching goal with those identified good boundaries. A missing boundary, for example, should have "near-by" good boundaries on both sides. Finally, they connect these pieces together and draw a "smooth" closed boundary. These terms and operations are part of the operators' knowledge and experience. The invention proceeds in a similar manner, but does so automatically, thus greatly speeding up the process.

In the preferred embodiment of the invention, for measuring heads, the system (preferably, the ID&M processor 128) partitions the binarized and filtered image into radially extending strips covering at least the portion of the image inside the $r_{ref}$ line. Although wider strips are possible, for reasons of precision and computational ease, each strip is preferably one pixel wide. In the assumed example, there are therefore 256 strips, each (with appropriate rounding) 360/256 degrees wide. In FIG. 5, one such strip is labelled 500.

For each angular strip, a transition vector is compiled and recorded in memory by examining the pixel values in the strip, which will be either "1's" or "0's", marking each transition between values, and recording for each block or group of "1's" how many contiguous "1's" are in the group, and also the radial endpoints of each group. Note that a group may have a single member, which will normally—but not necessarily—correspond to noise. Next, the invention marks as "non-boundary" groups any that are too narrow or too wide, defined either by experimentation and experience or by excluding groups whose widths deviate by more than an experimentally predetermined percentage from the widest contiguous groups that either contain the reference points 210, 212 or are closest to them. Remaining groups to the inside (in FIG. 5, to the left) of the $r_{ref}$ line are potential boundary groups.

The system then marks the positions of the right-most pixel in the contiguous group at the reference points. Next, the system uses any known method to calculate the amplitude of the approximating function that passes through these right-most points and best fits the potential boundary groups. Because the mainly elliptical head maps roughly to a sinusoid in polar coordinates, the approximating function is preferably also a sinusoid. Other known functions such as single polynomials, multiple splines (polynomial or otherwise), multiple sinusoids (for example, as the result of an FFT analysis), piecewise-linear functions (if short enough), and so on, may also be used. The measure of fit may be any conventional measure, such as the least-squares or minimum sum absolute difference (MSAD) to the right-most or center pixel of each group. Note that the period of the approximating sinusoid will be $4\pi$, since the closed curve 200 by definition extends over $4\pi$.

Once the system has determined the best-fit sinusoid (or other approximating function), it could calculate the length of the circumference simply by converting the sinusoid back into the Cartesian raster format, and then applying known numerical integration techniques for determining the path length of a curve. This would in many cases provide a measurement at least as good as what can be obtained using conventional measurement techniques. On the other hand, stopping at this point fails to adjust for the difference between measurement of the inner and outer circumference of the skull; normal HC measurements assume measurement of the outer circumference. The invention therefore preferably includes further intermediate steps to further identify and measure the outer boundary.

Once the best-fit sinusoid is determined, the system examines each strip and marks the potential boundary group (group of contiguous "1's") that the sinusoid passes through. If, for any strip, the sinusoid does not pass through such a group, then the system assigns a "1" at the pixel where it does cross the strip. This fills in any gaps that may occur in the binarized image.

It is known that the thickness of the skull is approximately constant around the typical cross sections of interest in ultrasound scans. The system therefore examines each strip where the sinusoid crosses it and stores how many pixels wide the boundary group is at that point. It then calculates the median or mean width of the "good" blocks, defined as those with the widest boundary blocks at the intersection points of the sinusoid. The number to be included in the median or mean calculation may be fixed, for example, the 32 widest blocks, or it may be variable and include, for example, all boundary blocks that are at least two pixels wide, thereby excluding strips that had a "gap" that was filled in. Assume, by way of example only, that the median width is five pixels. The system then examines each strip. For each strip with fewer than five "bright" (value "1") pixels at the intersection of the sinusoid, the system then assigns "1's" to five pixels centered at the pixel of intersection. At this point, the sinusoid is continuous and has a minimum width; each strip has a "boundary group" of pixels at least as wide as the median or mean pixel width, which the system assumes is the thickness of the skull The innermost pixel in each boundary group (located left-most as viewed in FIG. 5) corresponds to the inner surface of the skull; the outermost pixel corresponds to the outer surface. The 256 outer pixels represent the outer circumference of the skull. The system converts these back into Cartesian raster form and smooths them using a conventional filter, which may be a simple FIR filter, which operates as a low-pass filter to remove sharp bends and "spikes" from the curve. What remains is then a smoothed curve corresponding to the outer circumference of the head.

The system then displays this smoothed curve, preferably superimposed in color on the image of FIG. 2. Displaying this curve is advantageous since it gives the operator a chance to check whether the system's curve identification is reasonable. The processing system also calculates the path length of the smoothed approximating curve (equal to the HC) using known numerical integration routines. Then, it directs the display system to display the calculated value where the operator can easily see it, for example, along the bottom of the display screen 126. Note that by smoothing the innermost points of the boundary groups, the system could apply known numerical integration techniques to calculate the inner circumference. Similar numerical techniques may then also be used to calculate the cross-sectional area enclosed by the skull.

The system preferably also calculates and displays linear parameters such as BPD and OFD. If it is assumed that the operator has accurately placed the reference points 210, 212, the system can calculate OFD as the simple linear distance between these points. Alternatively, the system could use known techniques to find the longest line segment with endpoints on the circumference that is parallel to the line through the reference points.

The method preferred in the invention, however, also takes into account that the OFD should pass through or at least very near the center of mass of the head circumference. It first generates line segments that are parallel to the slope of the midline. If no midline slope can be accurately calculated, the system selects line segments parallel to the line connecting the user-input reference points. The system then identifies as the OFD the one among these line segments for which the linear distance between its endpoints divided by its perpendicular distance to the center of mass of the calculated circumference is greatest.

The preferred method for identifying and measuring images of generally straight structures is described below and initial substeps of that method may be used to identify the midline position and slope. As a simpler procedure, however, the system may take advantage of the placement of the reference points 210, 212 and procedure described above in which the inner delimiting circle 302 (FIG. 3) is known to enclose the midline.

The system may, for example, first assume that the midline slope is approximately equal to a reference slope, that is, the slope of the line connecting the reference points. Without converting to polar coordinates, the system may then separately store a representation of the portion of the image within the inner circle. To ease later calculations, this image portion is preferably rotated so that the line connecting the reference lines is horizontal, or at least in a predefined orientation. The system then applies to this image portion the steps of increasing contrast and morphologic filtering described above to create a binarized representation of the midline region.

The midline will then be a substantially horizontal pattern of bright pixels ("1's"). One way of determining the midline slope is then for the system to apply known optimization routines to determine the line that passes through, for example, the centroid of the horizontal pattern of bright pixels and best fits the bright pixels in some predetermined sense. Alternatively, the system may divide the image into a large number of vertical strips, for example, one pixel wide, scan on either side of the line connecting the reference points to locate the widest group of contiguous bright pixels for each strip, and then find the best-fit line connecting the center points of the widest groups. Regardless of the method used to determine the slope of the midline, once the approximating line is determined, the system may extend the line to the approximating curve for the skull, the outermost points of which may then be used to define the endpoints of the OFD.

To determine the BPD, the system may then find, using known numerical techniques, the longest line segment that is perpendicular to the OFD and has a proximal endpoint on the outer circumference and a distal endpoint on the inner circumference. The proximal outer point and distal inner point will normally be the points of strongest acoustic return and brightest boundaries for most ultrasound scans of the head.

The invention may, alternatively, use the boundary points of the approximating curve as starting points for a matched filter that operates on the unfiltered image data to identify outer and inner skull points, the distance between which is calculated and displayed as the BPD. As with the approximating circumferential curve, the calculated lines for OFD and BPD are preferably also displayed superimposed in color or otherwise clearly visibly on the unfiltered image to allow the user to check the reasonableness of the system's calculations.

Note that the system can identify the midline 208 without having calculated an approximating sinusoidal curve. Because of this, the invention can be adapted to a scheme in which the operator designates as initial reference points the apparent endpoints of the BPD instead of the OFD. A radius just smaller than half the distance between these reference points then defines the inner delimiting circle 302 and the radius of an outer delimiting circle can then be defined as a certain experimentally predetermined amount greater than that of the inner circle. The extension of the midline outward to the outer circle will then define the proper phase of the sinusoidal approximating curve.

Midline identification and extension can also be used to enable the system to identify and measure the head with only a single reference point input by the operator. Assume that the operator is instructed to mark as the reference point the approximate midpoint of the midline 208 of the displayed image of the head. The midline and its slope can then be identified as above. Assuming (requiring) that the user initiate measuring only when the entire cross-section of the head is visible on the display, the system can then set the diameter of the outer delimiting circle slightly less than the width of the display in the direction of the slope of the midline; alternatively, matching filters can be used along radial rays that start at the midpoint of the midline to get initial estimates of the location of the boundaries of the skull by locating bands or peaks of maximum brightness.

Knowledge of the maximum eccentricity of scanned heads can then be applied to determine the greatest likely proportional difference between the OFD and BPD; this ratio can then be used to determine within which radial range the brightness peaks should lie if they represent the skull. This in turn can be used to define the inner and outer delimiting circles and the invention can then proceed as above. The brightness peaks within the delimiting circles that lie on the extensions of the midline can then be used as the reference points for purposes of determining the proper phase of the approximating sinusoid.

The image of the fetus's abdomen is usually both weaker and less distinguishable from the surrounding tissue of the mother than is the fetus's head. Furthermore, the abdomen is usually either more truly circular than the head or is less regular. Two problems then arise. First, because the undeformed abdomen is often much more circular, the polar representation will be almost a straight line, so that the best approximating sinusoid will have a very small amplitude for all images of the abdomen. Moreover, because the abdomen may be so round, it will often be hard for the operator to accurately estimate the proper position of the reference points. Second, irregularity due to pressure from the mother's own stomach muscles, the force of the transducer against the mother's (and thus fetus's) belly, or both may make even the best sinusoidal shape a poor approximation.

Most sonographers are trained to mark as reference points a point directly behind the spine and the point opposite this point on the apparent abdominal wall. The system may use these points as the reference points 210, 212 for the purpose of establishing, for example, the radius of the outer delimiting circle 300, but it does not necessarily require such points to generate its approximating function.

Since the abdomen may be circular or irregular, as opposed to clearly elliptical, the preferred embodiment of the invention does not use an approximating sinusoid, although this is still possible. Rather, the invention preferably operates on the binarized image using other filters after the steps of contrast improvement and morphologic filtering. In order to fill in gaps in the filtered image with boundary blocks of bright pixels, the system may apply local approximating functions or splines to connect boundary blocks on either side of a gap. It is then possible for the system to generate a best-fit approximating function, such as a polynomial of appropriate order, whose path length is then calculated as above to determine AC. It is preferable, however, for the system to use a form of predictive filter, which is described below.

Assume that the image has been delimited and binarized, that its contrast has been improved, that is has been morphologically filtered, and that gaps have been filled in as described above, so that the system has created a continuous curve in polar coordinates. In one prototype of the invention, the system's predictive filter operated by accumulating in memory a "score" for a series of assumed boundary pixels. First, all pixels were assigned a starting score of zero. The system then selected the outermost (right-most, viewed as in FIG. 5) boundary pixel at the angle of one of the two designated reference points. It then added one to the score of this initial pixel. Next, the system examined the three pixels immediately below the initial pixel (the one at the same radius and the pixels one to either side of this one). One was added to the score of the outermost one of these pixels that was bright (had the binarized value of "1"). This pixel then formed the starting point for the evaluation of the next lower group of three pixels.

This process was then repeated until the system reached the lower edge of the polar display, at which point it "wrapped around" to the upper row of pixels and continued until it reached the initial pixel row (angle). The process was then repeated, beginning with the same initial pixel, but in the opposite direction ("up" instead of "down"). Then, the process of scoring was repeated in both directions beginning with the outermost boundary pixel at the angle of the other reference point. At the end of the four passes of scoring, four was the highest score a pixel could have accumulated; this indicated that, on all four passes, it was the outermost boundary pixel. Note that if any pixel had the score of four, then all other pixels at the same angle (in the same row) would have a score of zero. The invention then marked the positions of all pixels with a score of three or four (at most one at each angle) and then applied conventional numerical techniques to determine an approximating function such as a polynomial to best fit these "high scoring" pixels. This function, when convened back into Cartesian raster form, was then integrated as above to calculate circumference.

In order to determine diameter of the abdomen, head, or other mainly round body structure, without use of user-designated reference points or a midline reference, the invention may use known numerical optimization techniques to calculate the length of the longest line that connects any two points on the approximating curve, expressed in Cartesian coordinates. If the closed structure is not concave, most common algorithms will converge. Alternatively, the system may sequentially select initial points on the curve, then calculate the distance to opposing points within an interval around 180 degrees away from the initial point. Gradient methods may be used to speed the process of finding the longest chord from any given point. The initial point can then be changed, distances to the corresponding opposing points may be calculated, and the greatest chord distance found can be assumed to be the greatest diameter HC or AC.

Linear Structures

Figure 7:
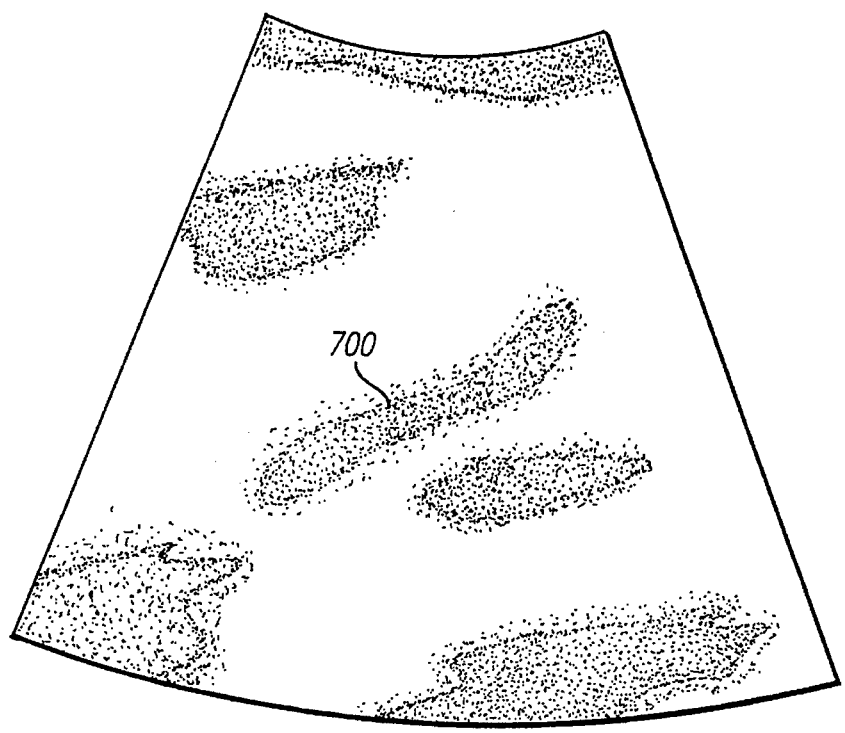
FIGS. 7 and 8 illustrate an ultrasonic scan of a mainly straight body structure such as a femur without and with, respectively, a user-selected reference point and system-generated windows.

FIG. 7 illustrates an ultrasound scan that shows a mainly straight body structure such as the femur 700.

The main steps the invention follows for measuring generally straight structures are as follows:

1) The assumed image of the structure is delimited to a portion of interest.
2) The approximate slope of the structure is calculated and is used to rotate the image to a computationally advantageous orientation. Note that the image need not be converted into polar form.
3) After optional but preferred sub-steps such as contrast enhancement and weighting, the image is binarized so that all image elements are preferably rendered as either fully "white" or fully "black."
4) The binarized image is filtered morphologically to further isolate the image elements that correspond to the generally linear structure.
5) The binarized image is preferably filled in to form a single contiguous bright region representing the structure.
6) An optimal approximating function is determined for the binarized structure.
7) The end points of the binarized structure are identified and the distance between them is measured and displayed.

These steps are explained below in the context of measuring a femur. Other mainly straight structures may be measured in an analogous manner.

Structure Delimitation

Figure 8:
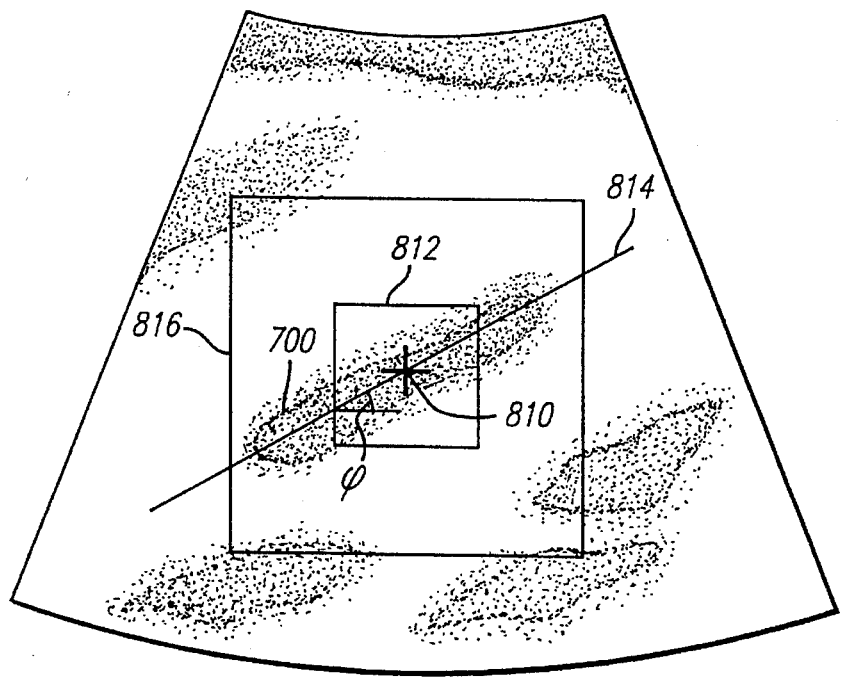

See FIG. 8. Using the trackball or mouse as before, the operator moves the cursor to a point on or near the displayed image of the bone and "clicks" or otherwise identifies the point as a reference point 810, which the system then preferably marks on the display screen. As is explained below, the preferred embodiment uses the single, user-input reference point 810.

The preferred system then internally delimits a preferably square or at least rectangular slope window 812, whose smallest dimension in pixels is known to be greater than the greatest possible width of the femur at the given approximate stage of gestation. This is preferably a preset or prestored value. In one prototype of the invention, for example, a 64×64 pixel window was found to be adequate for all typical femurs.

Using known numerical techniques, such as the well-known algorithms for linear regression, the system then calculates the parameters (slope and intercept) of the line 814 that best fits the data in the window in any chosen sense such as least-squares. In FIG. 8, the angle of the line 814 with respect to the lower edge of the window 812 is φ, which is a known function of the slope of the line 814.

Next, the system internally expands the search window to enclose the image of the femur. This may be done in various ways. For example, the maximum length of a femur at the given stage of gestation may be tabulated and used to determine the size of this enclosing window 816. As yet another alternative, the system may assume that the entire femur is visible in on the display screen and then simply expand the window until any corner of the window reaches the edge of the display area.

It is also possible (although, as will be seen below, neither necessary nor preferred) to instruct the operator to choose two reference points by clicking on what appear to be the endpoints of the displayed bone image. The enclosing window 816 can then easily be determined by making it just slightly (by a predetermined amount) wider than the distance between the points. The window 812 can then be generated, for example, as a window centered on the point half way between the reference points with sides, for example half as long as the sides of the enclosing window 812.

Operator input of endpoints would itself provide an immediate estimate of the femur length; indeed, this is the way femurs are typically measured in the prior art. It also provides an immediate estimate of the angle φ. It is known, however, that sonographers may have biases, such that they consistently over- or underestimate the position of the endpoints and thus the femur length. The invention would in this case use these user-input points as initial reference points but proceeds to delimit and filter the image to provide more consistent, bias-free and normally more accurate distance measurements.

Figure 9:
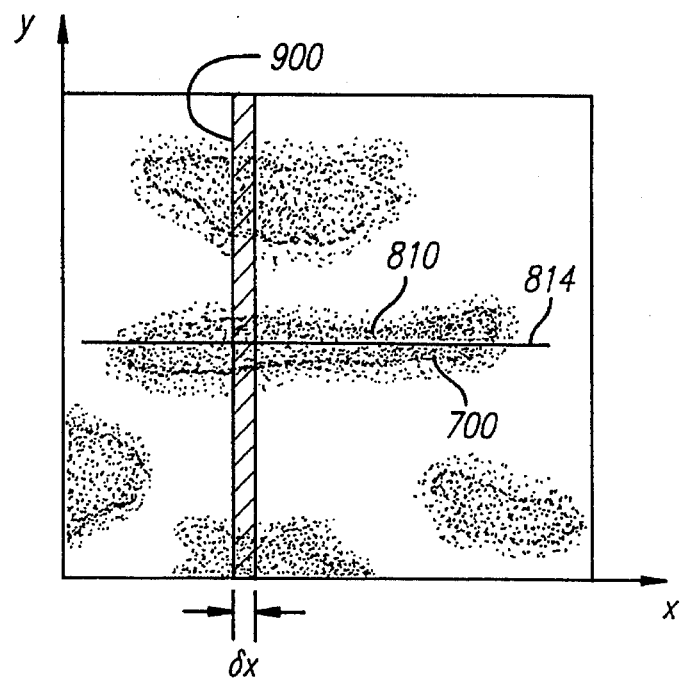
FIG. 9 illustrates a delimited and oriented (rotated) portion of the image in FIGS. 7 and 8.

The system then creates in memory a template (or uses dedicated memory positions to increase speed) for a rotated image portion. Such a template is illustrated in FIG. 9. The processing system then applies known transforms to rotate the portion of the image within the window 816 by φ, so that the line 814 is horizontal, viewed as in FIG. 9 (vertical works just as well, with appropriate indexing adjustments in calculations). At this point, the image of the femur is known to lie within the template and to extend roughly horizontally along the line 814.

Spatial Filtering

In the preferred embodiment, the system next applies a conventional two-dimensional low-pass filter to the entire region of the rotated template. One example of such a filter assigns to each pixel the value equal to the average (possibly weighted) of the values of the pixels in a region around and including the pixel itself.

Following this two-dimensional smoothing, a Gaussian, trigonometric, parabolic or triangular windowing filter is preferably applied over each vertical pixel line to further attenuate noise that lies away from the line 814. The window should therefore preferably be centered on the line 814, so that the point of least attenuation is at the pixel on the line 814. One such line is labelled 900 in FIG. 9. This is analogous to the radial weighting described above for closed curves, but in the case of linear structures, the template is not in polar coordinates.

Contrast Improvement

The preferred methods for contrast improvement for measurement of curved structures may also be used for measurement of linear structures and are therefore not described further here. Instead of a constant angle image strip 400 of angular width δθ as in FIG. 4 for a curved structure, the system applies the contrast function over the constant horizontal position strip 900 of width δx as in FIG. 9.

Image Binarization and Morphologic Filtering

The steps used for these procedures for measuring curved structures may also be used when measuring linear structures. These procedures are therefore not described further here. At the end of these steps, the processing system will have generated a binarized template of pixel data that includes the binarized image of the femur (or other mainly linear structure).

Structure Isolation

The goal of these steps is to transform the binarized template in such a way as to create a new template that contains a single contiguous set of "bright" pixels corresponding to the mainly straight body structure. This may be done using boundary identification procedures as described above for curved structures, with the lower boundary (viewed as in FIGS. 9 and 10) of the binarized straight image corresponding to the outer boundary of the binarized curved image. According to the invention, however, either of two other procedures are preferred, since they better take advantage of the knowledge that the structure to be measured here is mainly straight.

Figure 10:
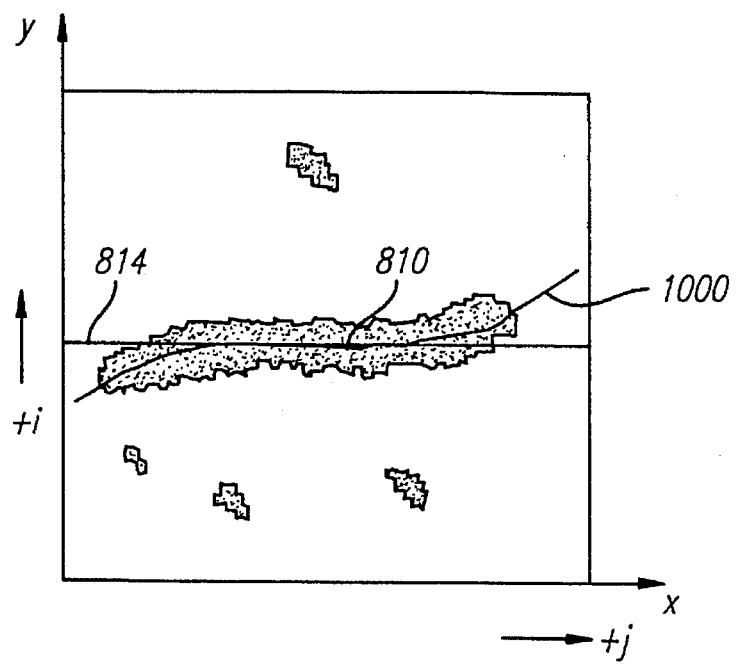
FIG. 10 shows the oriented image portion FIG. 9 in a binarized form.

In addition to FIG. 9, see FIG. 10, which illustrates a binarized image template. Note that, despite weighting, low-pass filtering, or both, the binarized image may still contain certain noise remnants. For ease of explanation only, it is assumed below that the terms "up," "down," "left," and "right" refer to the orientation shown in FIGS. 9 and 10.

In one prototype of the invention, to isolate the binarized image of the body structure, the system first generates a structure-isolating image template with the same dimensions as the binarized image template. For purposes of explanation, let $I_b(i,j)$ be the value of the binarized image template (which will include any noise remnants) for the pixel at row i and column j. The direction of positive increments of I and j are shown in FIG. 10: the indices (i,j) thus correspond to the position (y,x). Similarly, let $I_{iso}(i,j)=I_{iso}(y,x)$ be the values of the structure-isolating template. Note that these two templates are in registration. The initial value of all elements of $I_{iso}(i,j)$ is "0".

The center point of the line 814 within the boundaries of the template, or the pixel at the reference point 810, is assumed to lie within the image 700 of the structure and have the value "1", possibly as the result of the earlier image dilation. This pixel in $I_b$ is designated as a starting pixel. If this assumption is not true (the corresponding pixels are both "0's", probably by coincidence), then the system may, for example, examine pixels on either side of the chosen assumed center point and select as the starting pixel the nearest pixel on the line 814 that is surrounded by bright pixels. Let (p,q) be the index values of the starting pixel, that is, $I_b(p,q)=1$ is the starting pixel. The system then assigns the value "1" to the corresponding pixel in $I_{iso}(p,q)$.

Next, the system examines the pixel values of $I_b$ immediately above and below the starting pixel, that is $I_b(p+1,q)$, $I_b(p+2,q)$, . . . , $I_b(p-1,q)$, $I_b(p-2,q)$ Proceeding outward pixel by pixel, both up and down (increasing and decreasing j), it assigns the value "1" to each corresponding pixel of $I_{iso}$ until it encounters the first "0" pixel value of $I_b$ above and below the starting pixel, at which time the initialization phase is complete. At this point, the structure-isolation template will contain a single, one pixel-wide group of bright pixels, including the starting pixel; the vertical size of this group will be equal to the thickness, in the y direction, of the binarized image of the structure at the center point.

Then, the system successively increments the column index j and assigns $I_{iso}$ values as follows:

$I_{iso}(l,k+1) = $ "1" if:

$I_b(l,k+1) = $ "1" AND $\{I_{iso}(l,k) = $ "1" OR $I_{iso}(l+1,k) = $ "1" OR $I_{iso}(l-1,k) = $ "1"$\}$ $I_{iso}(l,k+1) = $ "0" otherwise.

In other words, a pixel in $I_{iso}$ is set to one only if the corresponding pixel in $I_b$ is a "1" and the pixel in $I_{iso}$ has at least one neighbor in the previous column that also is a "1". The system then increments the index j again and repeats this procedure until it reaches the boundary of the image. It then repeats this procedure to generate $I_{iso}$ values in the direction of decreasing j, in which case steps are decremented instead of incremented and neighboring pixels are defined to the right instead of to the left (viewed as in FIG. 10). Of course, the order in which the system constructs $I_{iso}$ (increasing or decreasing j first) is arbitrary.

At the end of this procedure, the template $I_{iso}$ will contain a binary representation of the structure, but will not have any bright values for any pixels that were not adjacent to at least one of the bright pixels of the binarized image. In particular, none of the binarized noise remnants that were separated by dark values ("0's") from the binarized structure image will be in $I_{iso}$.

As an alternative way of generating a contiguous pixel set in from which noise remnants have been eliminated, the system first creates a mask template that is in registration with the binarized image template (FIG. 10). In the initial condition, the only pixel in the mask template with the value "1" (the only bright pixel) is the starting pixel. This mask template is then dilated according to the morphologic rule that any pixel adjacent to any bright pixel itself is made bright. The dilated mask template is then registered with the binarized image template and a pixel-by-pixel logical AND operation is performed, with the result stored as the new mask template. The mask template is then iteratively dilated and AND'ed with the binarized template until the mask template is the same at the end of two consecutive AND operations, which indicates it has reached its filled-in steady state. The resulting image will be a contiguous set of bright pixels without "holes" and will correspond well to the image of the bone—any noise pixels that were not adjacent to bone pixels will have been eliminated by the AND operations.

Endpoint Identification and Length Measurement

Once the binarized image has been isolated and filled in, the system uses known methods to generate the curve 1000

(FIG. 10) that best approximates the binarized image in some predetermined sense, such as least-squares. As before, the approximating function or curve may be polynomial, trigonometric, piecewise linear, or belong to any other class; the choice of the type of approximating function may be made based on experimentation and experience.

In the case of femurs, a third-order polynomial has, for example, been found to provide good results. This is in part because fetal femurs very often have small but noticeable and opposite curvature at opposite ends, but are substantially straight over most of their length; third-order polynomials are well suited to approximate such shapes, although even higher-order polynomials may of course be used as long as conventional precautions are taken to avoid errors caused by the ill-conditioned nature of approximation using non-orthogonal, high-order polynomials.

Once the approximating function has been determined in relation to the binarized image, the endpoints of the bone may be selected simply to be, for example, the pixels located where the function "leaves" the binarized structure at either end. As an alternative, the system may simply mark as endpoint the pixels in the filled-in binarized image that lie farthest to the right and left, viewed as in FIG. 10. These methods, however, operate solely based on the binarized image, which may have been dilated or otherwise extended beyond the limits of the actual bone, although such deviation will normally be small.

In the preferred implementation of the invention, endpoints are selected by using a matched-filter template that moves over the gray-tone rotated image data (FIG. 9) after smoothing, along the curve of the approximating function, which is superimposed on the rotated image. Assuming by way of example the image orientations shown in FIGS. 9 and 10, the system first computes an included and an excluded average brightness value. The included brightness value is the average gray-tone value of all pixels in the rotated image whose corresponding pixel in the binarized image is bright; this value thus corresponds to the average brightness value of the bone. The excluded brightness value is the average value of the remaining pixels in the rotated image: this value thus corresponds to the average noise value.

The system generates the matched filter as a window whose width in the y-direction (see FIGS. 9 and 10) is roughly equal to the y-direction thickness of the binarized image, which can be determined, for example, either at the reference point 810, or by averaging along at least a portion of the binarized image along the curve 1000. The matched filter preferably has two halves, each with a pixel width determined by experiment, and which can be as small as one pixel. The system starts the matched filter at the reference point 810, keeps it centered vertically on the curve and moves the filter left and then right over the rotated gray-tone image until endpoints are identified. For the left-moving filter, the left half of the filter contains the excluded brightness values and the right half contains the included brightness value. For the right-moving filter the halves are switched.

For each position of the filter, the system computes, for example, the sum-absolute difference (SAD) value between the filter and the pixels it is over. The minimum SAD (MSAD) value will occur when the filter is centered over the endpoints of the image of the bone. These pixels are then marked and are preferably displayed as such.

Once the endpoints are identified, the system calculates and displays the linear distance between them, which is the conventional definition of femur or humerus length. The system preferably also displays markers at the calculated endpoints and a line connecting them; as before, this gives the operator a visual confirmation of the reasonableness and reliability of the measurement. Using known integration techniques the system could, however, instead or in addition calculate the non-linear path length of the bone along the line 1000 between the endpoints.

For both mainly round and mainly linear structures, the system may store in memory, print out, or otherwise record the approximating functions and the calculated measurement parameters (OFD, BPD, HC, AC, FL, HL, etc.), instead of or in addition to displaying them on the display screen for the user to view.

We claim:

1. A method for measuring human body structures using ultrasound comprising the following steps:

generating and displaying an image frame as a pattern of pixels, each pixel having a brightness value corresponding to an echo signal from a corresponding portion of an interrogation region of the human's body, which includes the body structure, the image frame including a structure frame portion corresponding to the body structure;

designating a general geometry feature of the displayed body structure and at least one measurement parameter associated with the designated geometry feature;

selecting at most two reference points associated with the displayed body structure;

filtering the displayed image to identify the structure frame portion;

generating an approximating function corresponding to the designated measurement parameter; and calculating each measurement parameter as a predetermined function of the approximating function.

2. A method as in claim 1, further including the step of displaying the calculated measurement parameters.

3. A method as in claim 1, in which the step of designating a general geometry feature comprises designating substantially curved, closed body structures, the measurement parameters thereby comprising at least one of the group consisting of circumference and at least one predefined diameter.

4. A method as in claim 1, in which the step of designating a general geometry feature comprises designating a substantially linear body structure, the measurement parameter thereby being length.

5. A method as in claim 1, further including the following steps:

delimiting a delimited image portion of the displayed image as a function of the reference points;

binarizing the delimited image portion; and morphologically filtering the binarized, delimited image portion, the approximating function thereby approximating the morphologically filtered image portion.

6. A method as in claim 5, further including the step of increasing the contrast of the delimited image portion before the step of binarizing.

7. A method as in claim 5, further including the following steps:

determining a reference line, which may be curved, for the delimited image; and weighting the pixel brightness values of the delimited image as a predetermined function of their position relative to the reference line before the step of binarizing.

8. A system for measuring human body structures using ultrasound comprising:

ultrasonic transducer means for generating an image frame as a pattern of pixels, each pixel having a brightness value corresponding to an echo signal from a corresponding portion of an interrogation region of the human's body, which includes the body structure, the image frame including a structure frame portion corresponding to the body structure;

a display for displaying the image frame;

geometry selection means for designating a general geometry feature of the displayed body structure and at least one measurement parameter associated with the designated geometry feature;

reference selection means for selecting at most two reference points associated with the displayed body structure; and processing means for filtering the displayed image to identify the structure frame portion;

for generating an approximating function corresponding to the designated measurement parameter; and for calculating each measurement parameter as a predetermined function of the approximating function.

* * * * *